(12) United States Patent
Cooper et al.

(10) Patent No.: US 8,799,286 B2
(45) Date of Patent: Aug. 5, 2014

(54) SYSTEM AND METHOD FOR ORGANIZING AND DISPLAYING OF LONGITUDINAL MULTIMODAL MEDICAL RECORDS

(75) Inventors: James W. Cooper, Wilton, CT (US); Youssef Drissi, Ossining, NY (US); Shahram Ebadollahi, White Plains, NY (US); Anthony Tom Levas, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 582 days.

(21) Appl. No.: 12/256,858

(22) Filed: Oct. 23, 2008

(65) Prior Publication Data

US 2010/0106522 A1    Apr. 29, 2010

(51) Int. Cl.
*G06F 7/00* (2006.01)
*G06F 17/30* (2006.01)

(52) U.S. Cl.
USPC ................................ 707/738; 382/132; 705/3

(58) Field of Classification Search
None
See application file for complete search history.

(56) References Cited

U.S. PATENT DOCUMENTS

| | | | |
|---|---|---|---|
| 2003/0009295 A1* | 1/2003 | Markowitz et al. | 702/20 |
| 2005/0038342 A1* | 2/2005 | Mozayeni et al. | 600/454 |
| 2005/0246366 A1* | 11/2005 | Kouchi et al. | 707/102 |
| 2007/0198564 A1* | 8/2007 | Blackstone et al. | 707/101 |
| 2008/0040151 A1* | 2/2008 | Moore | 705/2 |
| 2008/0270120 A1* | 10/2008 | Pestian et al. | 704/9 |
| 2009/0136111 A1* | 5/2009 | Jabri et al. | 382/132 |
| 2009/0299766 A1* | 12/2009 | Friedlander et al. | 705/3 |
| 2010/0036676 A1* | 2/2010 | Safdi et al. | 705/2 |
| 2010/0080427 A1* | 4/2010 | Yeluri et al. | 382/128 |

* cited by examiner

*Primary Examiner* — Dung K Chau
(74) *Attorney, Agent, or Firm* — Tutunjian & Bitetto, P.C.; Preston J. Young

(57) ABSTRACT

A system and method for processing data includes organizing medical information in a concept frame data structure, which is adapted to include medical measurements and related metadata. The medical information is analyzed to extract further information using information extractors and to store extracted medical information in the concept frame data structure. References are stored to appropriate visualization methods along with an associated concept in the concept frame data structure.

23 Claims, 6 Drawing Sheets

SYSTEM AND METHOD FOR ORGANIZING AND DISPLAYING OF LONGITUDINAL MULTIMODAL MEDICAL RECORDS

BACKGROUND

1. Technical Field

The present invention relates to data organization and more particularly to a system and method for organizing patient data to provide coherence to related information in disparate sources.

2. Description of the Related Art

Currently, multi-modal medical records (various modalities of medical imaging, different types of text reports, and laboratory data) are stored in Electronic Patient Records (EPR). EPR stores and manages all patient related data in their native digital file format (video, image, text, etc.), which does not satisfy all the information needs of the users of the data (clinicians, nurses, etc.) for considering the special characteristics of different patients. Clinicians and other users of data in health-care institutions are interested in obtaining information concerning different anatomical and pathologic concepts (e.g. tumor, edema region, mitral valve, etc.) to better assess the patient's condition. However, the heterogeneous sources of data lack any coherent organization of their content around the relevant medical concepts that are observable within them.

Relationships between relevant concepts and their associated attributes (color, size, density, texture, dosage, etc.) across an artifact are also not easily obtained. Furthermore, the lack of proper concept-based organization of the multi-modal medical records prevents the users of such records from tracking the evolution of a concept through time, and does not allow one to study the variations of the characteristics of a set of concepts of interest across a cohort of patients for decision support tasks.

Electronic Patient Records (EPR)—e.g., Siemens™ system, VISTA™, WebCIS™, etc. have the following shortcomings. Only document and file level access to patient records is provided through these systems. These systems do not provide access to concepts and their linkage to their manifestations in different modalities embedded in the documents. Formats used for keeping medical records are generic and do not reflect personal characteristics of the patients. It is very difficult to evaluate temporal change and monitor the evolution of the characteristics of conditions or occurrence of new ones for a given patient across time. Because of lack of access to concepts and linkage, it is difficult to compare different patients with respect to certain attributes of medical problems for population studies.

A Generic Electronic Health Record (GEHR) is a refined version of the above solution, in the sense that medical data are captured and stored based on concepts. Although this standard provides access to concepts, it does not provide linkage of the concepts at any level to their multi-media/modal manifestations. Also, multi-media data are regarded as a whole document in GEHR, and access to their spatio-temporal content structure is not provided or envisioned.

Research in concept-mapping is restricted to mapping concepts spotted in articles or text documents to existing ontologies such as UMLS, or GO (Gene Ontology). The mapping process does not consider the multimodal nature of the medical records, and the concept graphs that are constructed based on text documents only. Further, such systems do not attempt to deal with the semantic meanings inherent in these text documents.

SUMMARY

The present invention provides a system and method for coherent organization of all patient related multi-media medical records around a "personalized concept-graph" structure. This new scheme for organizing medical records aims at addressing the above mentioned problems.

A system and method for processing data includes organizing medical information in a concept frame data structure, which is adapted to include medical measurements and related metadata. The medical information is analyzed to extract further information using information extractors and to store extracted medical information in the concept frame data structure. References are stored to appropriate visualization methods along with an associated concept in the concept frame data structure.

A system and method for processing data includes organizing medical information in a concept frame data structure, which is adapted to include medical measurements and related metadata; analyzing the medical information to determine relevant analytics that can be applied to the concept frame to extract further information; and applying the analytics to the concept frame to generate a concept graph for a given patient event, the concept graph representing related medical information existing in different modes, which are associated with a given concept for the concept frame.

An analytic processing system includes an analytics repository configured to store one or more analytical programs to analyze medical information. A workflow mediator is implemented in software on a program storage media and configured to receive information source data structures and concept frame data structures to build an analysis request. A pipeline manager is implemented in software on a program storage media and configured to receive the analysis request and determine relevant analytics from the analytics repository to be used to analyze the information source data structures and the concept frame data structures. An unstructured information management architecture (UIMA) is configured to classify, organize and extract additional data from medical information in the information source data structures and the concept frame data structures and render the medical information in a graphical context.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
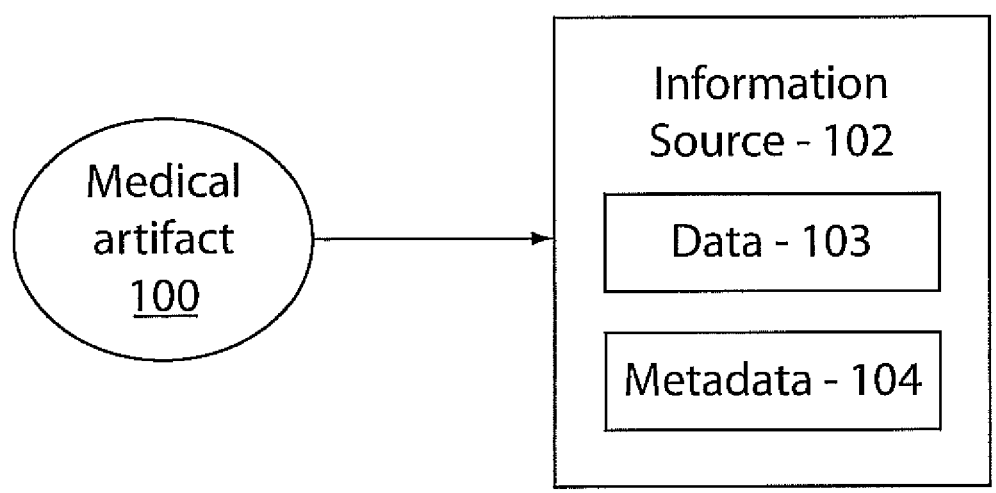
FIG. 1 is a diagram showing an information source data structure in accordance with the present principles.

Systems and methods are provided for automatically extracting medical concepts, e.g., from text, lab and image data (X-Rays, magnetic resonance (MR) imaging, positron emission tomography (PET) scans, etc.) of different modalities, that have been previously defined in a medical ontology, as well as linking (relating) these medical concepts across a set of artifacts that comprise a context of a current medical visit of a patient. The present approach provides a set of innovative ideas to accomplish this.

In accordance with particularly useful embodiments, a declarative data structure is provided for medical concepts called a ConceptFrame that provides knowledge-guided extraction of medical concepts (along with their associated attributes) from multi-modal medical artifacts (such as magnetic resonance images and textual notes and lab reports). A concept is a term describing a pathological or anatomical entity. "Brain tumor" and "mitral valve" of the heart are examples of concepts. ConceptFrame and concept frames will be used synonymously throughout this disclosure.

Medical artifacts and associated meta-data needed for automated analysis are aggregated in a data structure called an Information Source. A Concept Based Analysis System uses the knowledge expressed in ConceptFrames and Information Sources to coordinate the application of relevant analytics for the extraction of concepts and associated attributes. In addition, ConceptFrames include meta-data relevant to knowledge-guided visualization, quantification and representation of extracted concepts and their respective attributes.

A network of the ConceptFrames linked to each other (guided by available or expert-constructed ontologies) will form a Concept-Graph Instance for each patient visit, groups of visits or time frames. Only concepts that are relevant and appear in multimodal artifacts for that patient will be present in each patient's Concept-Graph Instance.

As new studies are performed on a patient in subsequent visits, new Concept-Graph Instances are created. These Concept-Graph-Instances can be compared over time to form a current understanding of the patient's condition. This results in the notion of an Information Cylinder, which is the temporal extension of the patient's medical record as organized around the evolving concept-graphs. The set of all Concept-Graph-Instances for a patient comprise the patients Personal Concept History. This set of data structures and system architecture will be described herein.

The systems and methods provide multiple advantages with respect to managing multi-modal medical records. These include providing users of the patient's medical records with efficient access points to the content of those records at the concept level. Another advantage includes summarizing all multi-modal mentions of a concept and its attributes in a single ConceptFrame at any given point in time. Links between concepts, provided by the concept graph, can be used to navigate the medical records of the patient at the concept level. The concept-based organization of the patient records using the personalized concept-graph as the template, permits users to obtain different "views" of the patient's medical records for different tasks and contexts, through interaction with the concept-based organization via proper visualization, browsing, and summarization engines that reveal the relevant subsets of the concept-graph.

The organization of the patients' multimedia medical records using the concept-graph, provides an efficient framework for concept-based linking of the patients' records to contextual information derived from heterogeneous resources (analytics) for applications such as "decision support systems," or education. Examples of such resources include, electronic medical textbooks, online medical articles, information extracted from the world wide web, specialized medical knowledge bases, e.g., genotype and phenotype information, population studies, etc.

A useful form for organizing medical records, provides an efficient framework for the study of the evolution of the attributes of any given concept through time in the context of the "information cylinder." This organization of the medical records provides a framework for population studies through graph-based analysis of the collection of medical records across different patients.

Embodiments of the present invention can take the form of an entirely hardware embodiment, an entirely software embodiment or an embodiment including both hardware and software elements. In a preferred embodiment, the present invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Referring now to the drawings in which like numerals represent the same or similar elements and initially to FIG. 1, a medical artifact 100 is illustratively shown with an illustrative Information Source 102. An Information Source 102 is a data structure that aggregates a specific medical artifact (e.g., data 103, which may include images, text, or other information), such as a magnetic resonance imaging (MRI) file, CT scan file, X-ray file, sonogram file, etc., along with all other relevant metadata 104 needed for analyzing the artifact to extract the relevant medical concepts and their associated attributes. For example, an MR Information Source 102 may include the following possible metadata:

| Type: | MR |
| --- | --- |
| SubType: | T1 |
| Patient ID: | 1168532 |
| View: | Coronal |
| Anatomical Region: | Brain |
| Date: | May 23, 2006 |

Figure 2:
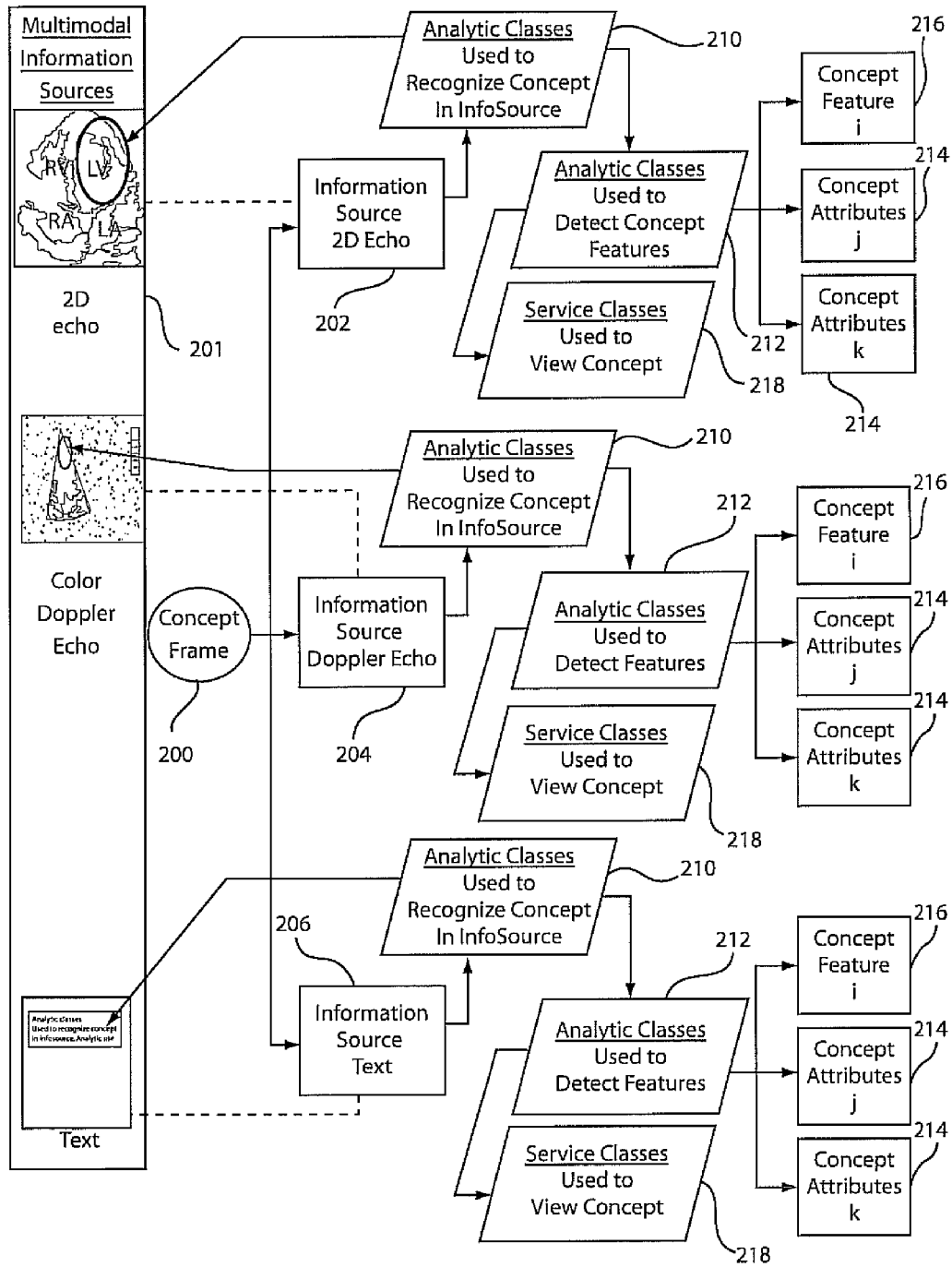
FIG. 2 is a block diagram showing construction of a concept frame in accordance with the present principles.

Referring to FIG. 2, a ConceptFrame 200 is illustratively depicted. A ConceptFrame 200 is an organizing data structure (declarative in nature) that aggregates relevant information (metadata) for a single medical ontological concept such as "mitral valve" as manifested in different media and modalities of information sources.

A multimodal information source 201 is employed to summarize all multi-modal mentions of a concept and its attributes in a single ConceptFrame 200 at any given point in time. ConceptFrame 200 aggregates: 1. Information sources in which the medical concept can be detected. For example, FIG. 2 shows information sources such as 2D echocardiogram 202, color Doppler echocardiogram 204 and clinical text 206 associated with the concept of "mitral valve" in a cardiac scenario. 2. Analytics 210 that can be used to recognize the concept in a specific information source. For example, computer vision analytics for identifying a tumor in the magnetic resonance image (MRI) of the patient's brain or identifying the location of the mitral valve in a cardiac patient. 3. Analytics 212 for deriving attributes of the concept. For example, shape, size, and other characteristics of the brain tumor as it appears in the MRI, or the speed of mitral valve opening and closing operation as it appears in the echocardiogram video. 4. Constraints that specify the order of processing for the analytics (210 and 212). That is, e.g., analytics A and B must run before analytic C. Other constraints are also contemplated. 5. Attributes 214 of the concept that may be needed in the analysis of this Information Source that come from processing of other Information Sources related to this concept. For example, a concept and its attribute derived from the clinical notes (text data) might trigger an analytic engine on the MRI of the patient, or a feature 216 (image characteristics) obtained from MRI of type T1 might be used in identifying the instance of a concept in MR of type FLAIR. 6. A list of software services 218 that can be used to visualize, quantify, and characterize the medical concept and associated attributes from each of the Information Sources.

Some general purpose analytics (e.g., edge detection analytics for images) are reusable across different information sources while others may be very specific to a particular information source and concept. Analytics (210, 212) may be aggregated and sequenced to accomplish complex processing using, e.g., the UIMA framework (Unstructured Information Management Architecture). The UIMA system, developed by IBM, has been released into open source, and provides a complete framework for developing a chain of text recognizers, called annotators, which can be used to construct systems for highly sophisticated text analytics.

UIMAs are software systems that analyze large volumes of unstructured information to discover knowledge that is relevant to an end user. UIMA is a framework for developing such applications. An example UIM application might ingest plain text and identify entities, such as persons, places, organizations; or relations, such as works-for or located-at. UIMA enables such an application to be decomposed into components, for example "language identification"→"language specific segmentation"→"sentence boundary detection"→"entity detection (person/place names etc.)". Each component implements interfaces defined by the framework and provides self-describing metadata via XML descriptor files. The framework manages these components and the data flow between them. Components are preferably written in Java or C++; the data that flows between components is designed for efficient mapping between these languages. UIMA additionally provides capabilities to wrap components as network services, and can scale to very large volumes by replicating processing pipelines over a cluster of networked nodes.

Figure 3:
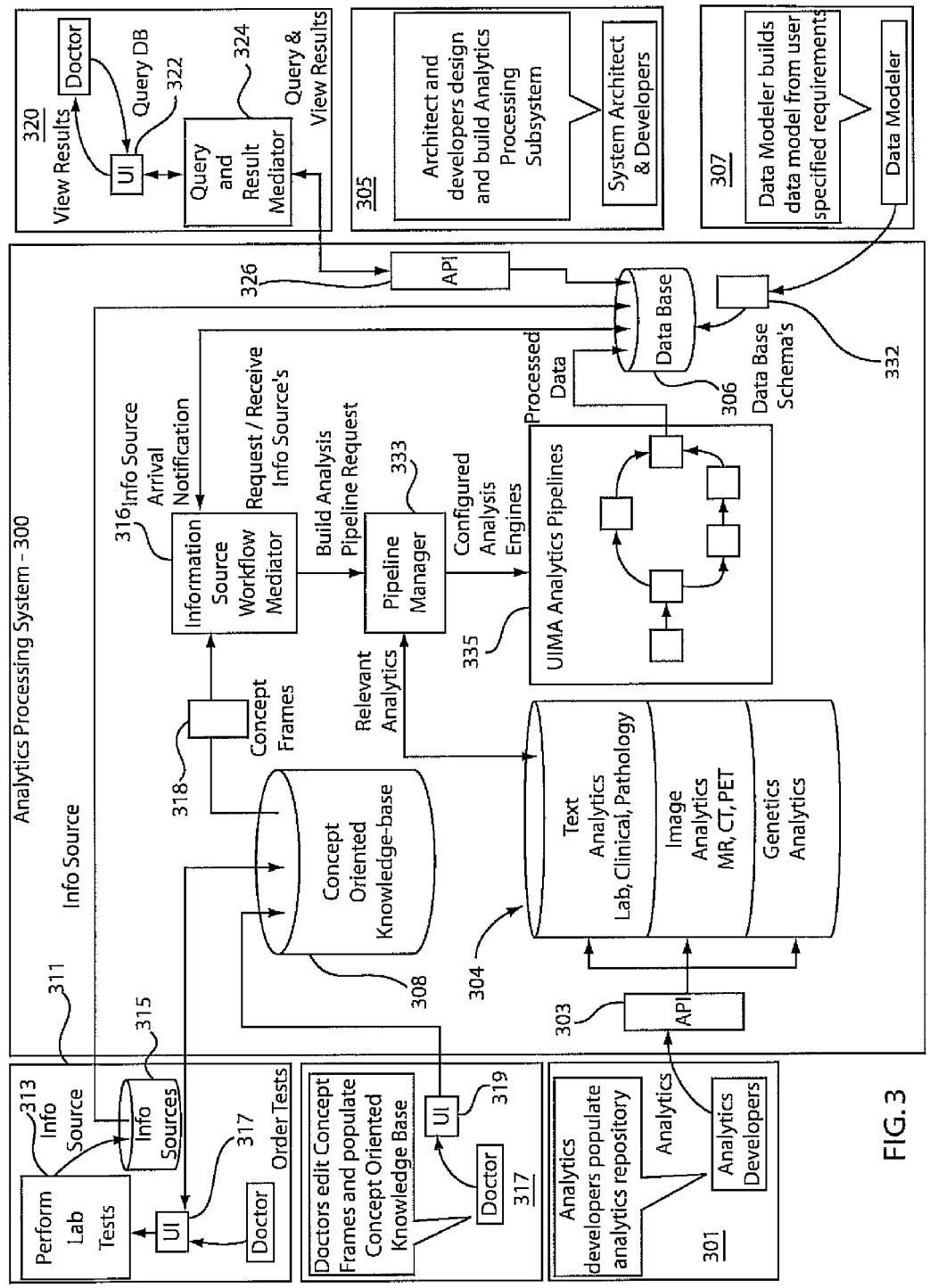
FIG. 3 is block/flow diagram showing an analytics processing system in accordance with the present principles.

Referring to FIG. 3, architecture of a Concept Based Analysis System 300 is illustratively shown in accordance with an exemplary embodiment. An Analytics Repository 304 can be accessed, aggregated, sequenced and applied to various incoming artifacts. Repository 304 may include text analytics (lab, clinical, pathology, etc.), image analytics (MR, CT, PET, etc.), genetics analytics and any other form of analyzed data. Analytics may take the form of software applications. Repository 304 is populated by analytics developers 301 using an application program interface (API) 303. Repository 304 includes analytics for analyzing medical information in the form of provided data structures (e.g., ConceptFrames and/or Information Sources).

An Artifact and Results Database 306 includes stored info sources 315. The database 306 stores original raw text, lab and image data and analyses performed on the data to extract further data in addition, metadata regarding each measurement are stored in this database 306, including the time of each measurement, so it is possible to produce of a timeline of the patient's progress with respect to each analysis that was performed.

The database 306 may be created by developers 305 and data modelers 307 to build data models 330 from user specifications using database schemas 332, which may be user specified as well. When a new information source is entered in database 315, the information source is added to database 306. An arrival notification is sent to an information source workflow mediator 316. The mediator 316 may request new information sources, and the information sources are sent to the mediator 316 to manage the workflow.

A Concept Oriented Knowledge-Base database 308 includes a representation of a rich data model of the measurements and analyses termed ConceptFrames. This data model is developed in consultation with physicians, clinicians and knowledge engineers 317 so that the relationships between these analytics are accurately represented. Test information and user edits from user interface 319 populate the Knowledge-Base database 308. Conceptframes 318 are generated or enhanced and stored in the Knowledge-Base database 308.

In block 311, a doctor orders a series of tests in block 313 (e.g., MR, CT, PET, lab work, etc.) and may specify the results to be extracted, such as brain tumor, edema, necrosis and the like. These desired "concepts" are stored as info sources in a database 315 and provided to database 306 as results become available. A user interface 317 is used to access a Knowledge-base 308. A Workflow Mediator 316 accesses ConceptFrames 318 from Knowledge-base 308. The Mediator 316 requests the necessary analytics to produce the required information by building an analysis pipeline request which is sent to a pipeline manager 333. The pipeline manager 333 manages the flow of data from the analytics repository 304. In addition, the ConceptFrames 318 themselves may specify particular information (such as drug dosages, and vital statistics) which is to be extracted automatically by the mediator 316 for use with the pipeline manager 333. The information sources and concept frames are employed to identify which analysis engines or resources are needed to configure an electronic patient record. The analytics are identified by the pipeline manager 333 so that complex processing of the user profile may be performed using an UIMA analytics pipeline 335. The UIMA 335 processes the information in accordance with rules, standards and/or user preferences to accumulate a patient history. The patient history is preferably graphical in nature. The processed data is stored in database 306.

In block 320, accessing of accumulated lab and analytic information by the physician or other clinician using appropriate visualization software (e.g., user interface 322) is performed. The user employs a query and result mediator 324 to query database 306 through an application program interface (API) 326. ConceptFrames or an entire profile for a patient are made available pursuant to the user query.

The set of ConceptFrames compiled and populated for a given patient can be assembled in a graph format (Concept Graph) at a given point in time. A linkage among Concept-Frames is obtained from the relationships between the concepts they represent as indicated in available ontologies. Examples of ontologies include the "Foundational Model of Anatomy," "Unified Medical Language System (UMLS)," "Medical Subject Headings," etc. The proper ontology is based on the domain of application and the set of concepts of interest for a given task and use case scenario. At a given point in time, certain ConceptFrames may be left alone without any connection to others. As time progresses and new studies are obtained for the patient, new concepts might become available, new attributes might become relevant, and new linkages among ConceptFrames may be established.

Figure 4:
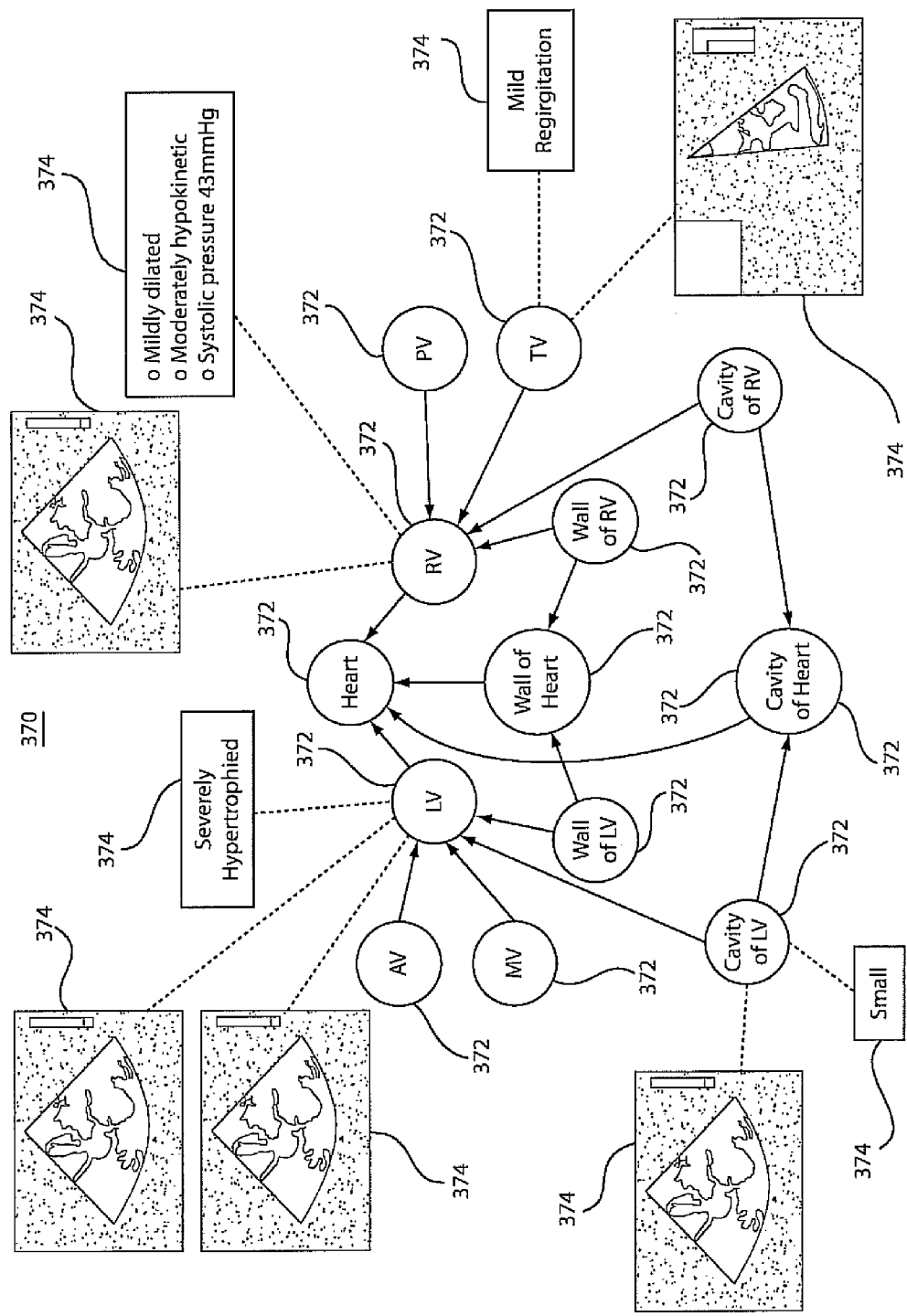
FIG. 4 is a diagram showing a concept graph in accordance with the present principles.

Referring to FIG. 4, a concept graph 370 is illustratively shown. A concept-graph 370 includes two types of nodes and edges. The concept nodes (e.g., nodes 372) represent a given concept of interest (e.g., "edema", mitral valve 372), whereas an instance node 374 represents the manifestation of the concept (media snippet) in a given medium/modality (e.g. "edema" in magnetic resonance image, heart images, text, etc.) with its associated attributes (e.g. "volume"). An instance node is connected to its relevant concept node via an edge (broken lines connecting nodes 372 and 374 or node 410 to 408 in FIG. 5). Two concept nodes are connected if based on a given ontology they have a relationship. For example, the node for concept "mitral valve" (MV) is connected to the node for concept "left ventricle" (LV). Other nodes 372 include portions of the heart such as valves (AV, MV, PV, TV), walls (heart, LV wall, right ventricle (RV) wall) and cavities (e.g., heart, LV, RV). FIG. 4 displays a concept-graph in the context of cardiac data organization at a given point in time. Attributes of such a concept might vary with time. This is illustrated by the broken arrows 426 in FIG. 5 connecting the same concept between two time points (402 and 404).

Figure 5:
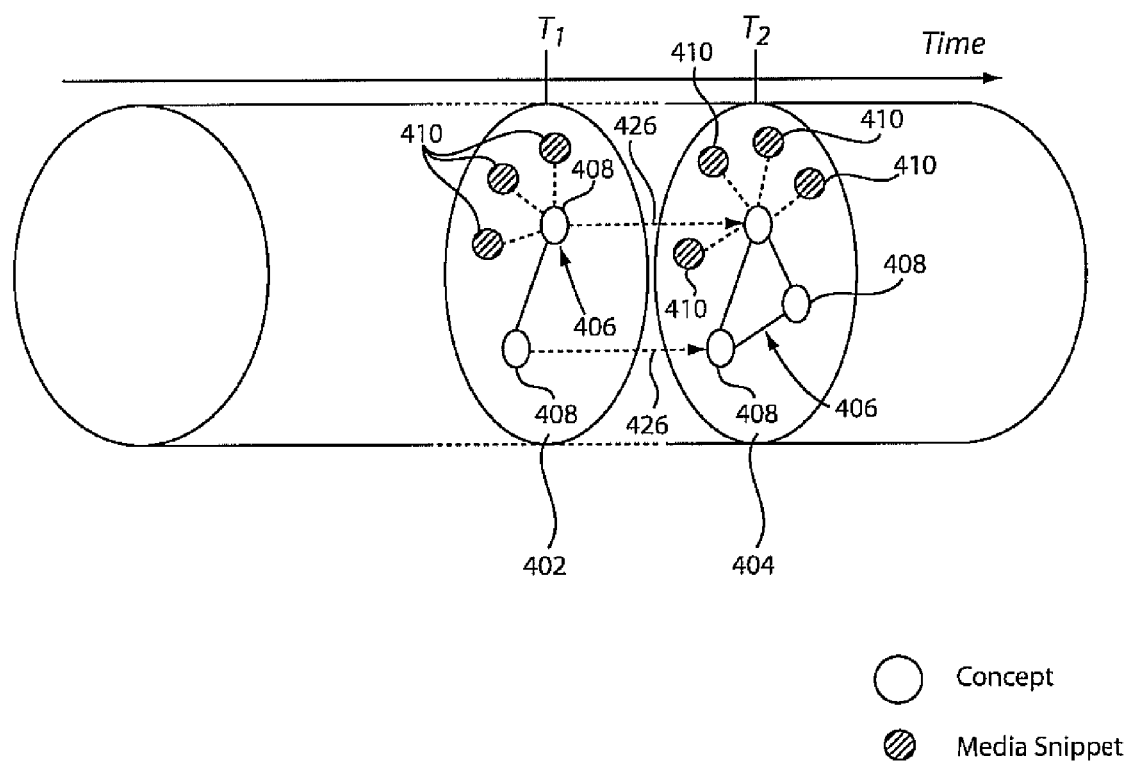
FIG. 5 is a diagram showing an information cylinder in accordance with the present principles.

Referring to FIG. 5, an Information Cylinder 400 extends a Concept Graph 402 corresponding to time $T_1$, and Concept Graph 404 corresponding to time $T_2$ for a patient to the temporal domain. New ConceptFrames 406 (represented here as the combination of concepts 408 and media snippets 410 depicted as nodes) might become relevant as time progresses (consecutive visits by the patient to the health-care institute, etc.).

Figure 6:
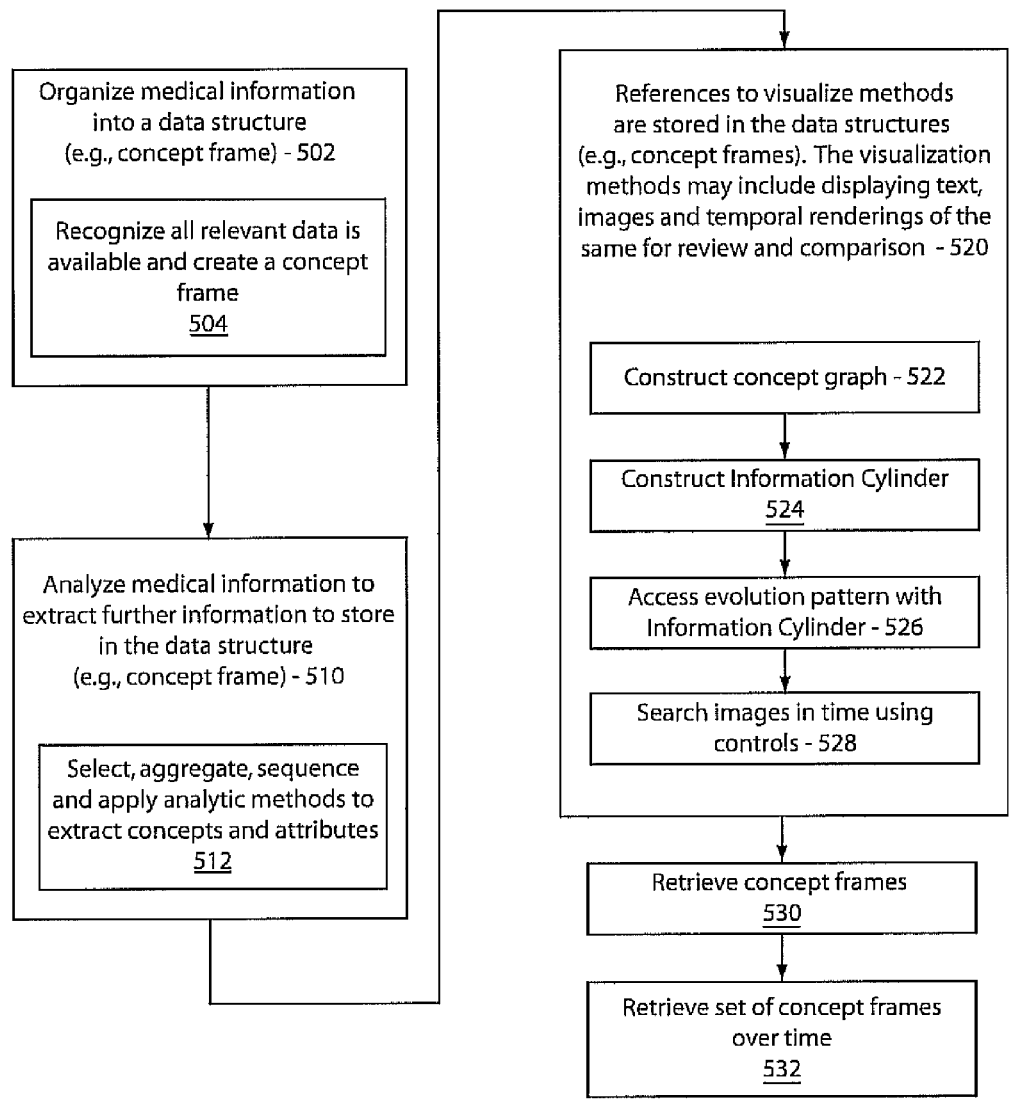
FIG. 6 is a block/flow diagram showing a system/method for processing medical data for electronic patient records in accordance with the present principles.

Referring to FIG. 6, a block/flow diagram showing a system/method for processing data is illustratively depicted. In block 502, medical information is organized in a data structure (e.g., concept frame), which is adapted to include medical measurements and related metadata. The medical information includes one or more of text, images, and lab data, and the metadata includes one or more of date, physician, and laboratory.

In block 504, in accordance with a set of events, a mechanism is provided that recognizes that all needed events (or information sources) have been performed and are available in a database. Then, medical results associated with the events are organized into one or more concept frames.

In block 510, the medical information is analyzed to extract further information using information extractors and the extracted medical information is stored in the concept frame. In block 512, medical information being organized includes selecting, aggregating, sequencing and applying relevant analytic methods to each piece of medical information in a database to extract concepts and attributes from the medical information to store extracted concepts and attributes as the concept frame.

In block 520, references to appropriate visualization methods are stored along with an associated concept in the concept frame. Storing references to appropriate visualization methods may include relating concept frames at a given time according to knowledge extracted from medical ontologies to construct a personalized Concept-Graph of a patient at that time in block 522. Storing references may include providing temporal records of the patient in an Information Cylinder, which is a sequence of Concept-Graphs, where each element of the sequence represents a different patient event in block 524. Storing references may include providing access to an evolution pattern of an attribute of a concept through interaction with the Information Cylinder in block 526. In block 528, a user may search slices or portions of images from different time points using a control, such as a virtual slider control, to visually scroll through the Information Cylinder.

The visualization methods may include one or more of: displaying extracted medical text information; displaying extracted medical image information; displaying extracted medical text information over time, so that a user can select a time point and view the relevant text information organized in categories; displaying extracted medical image information over time, so that the user can select a time and view relevant image information; and displaying highlighted regions of images showing regions of the image where particular medical information has been detected. Another visualization method may include displaying pairs of images from different time points so that the images can be compared in real time. This can be performed by medical personal to compare images taken at different times, e.g., compare tumor sizes or the like.

In block 530, concept frames may be retrieved from a database relevant to a patient visit. In block 532, a set of concept frames may be retrieved over a period of time to permit display of changes in a patient's condition.

Having described preferred embodiments of a system and method for display and analysis of time evolution of medical text and image data (which are intended to be illustrative and not limiting), it is noted that modifications and variations can be made by persons skilled in the art in light of the above teachings. It is therefore to be understood that changes may be made in the particular embodiments disclosed which are within the scope and spirit of the invention as outlined by the appended claims. Having thus described aspects of the invention, with the details and particularity required by the patent laws, what is claimed and desired protected by Letters Patent is set forth in the appended claims.

What is claimed is:
1. A method for processing data, comprising:
organizing medical information in a non-transitory computer readable storage medium in a concept frame data structure, which organizes the medical information for a single pathological or anatomical entity and includes medical measurements and related metadata;

analyzing the medical information to extract further information using information extractors and storing extracted medical information in the concept frame; and storing references to appropriate visualization methods along with an associated concept in the concept frame by relating concept frames for different pathological or anatomical entities at a given time according to knowledge extracted from medical ontologies to construct a Concept-Graph of a patient at that time.

2. The method as recited in claim 1, wherein the organizing medical information includes organizing content of one or more of text, images, and lab data.

3. The method as recited in claim 1, wherein the organizing medical information includes organizing metadata including one or more of date, physician, and laboratory.

4. The method as recited in claim 1, wherein the storing references to the appropriate visualization methods includes:
providing temporal records of the patient in an Information Cylinder, which is a sequence of Concept-Graphs, where each element of the sequence represents a different patient event; and
providing access to an evolution pattern of an attribute of a concept through interaction with the Information Cylinder.

5. The method as recited in claim 1, wherein the visualization method includes one or more of:
displaying extracted medical text information;
displaying extracted medical image information;
displaying extracted medical text information over time, so that a user can select a time point and view the relevant text information organized in categories;
displaying extracted medical image information over time, so that the user can select a time and view relevant image information; and
displaying highlighted regions of images showing regions of the image where particular medical information has been detected.

6. The method as recited in claim 1, wherein the visualization method includes:
displaying pairs of images from different time points so that the images can be compared in real time.

7. The method as recited in claim 1, wherein the organizing medical information includes selecting, aggregating, sequencing and applying relevant analytic methods to each piece of medical information in a database to extract concepts and attributes from the medical information to store extracted concepts and attributes as a concept frame.

8. The method as recited in claim 1, further comprising:
retrieving concept frames from a database relevant to a patient visit.

9. The method as recited in claim 1, further comprising:
retrieving a set of concept frames over a period of time to permit display of changes in a patient's condition.

10. A non-transitory computer readable storage medium comprising a computer readable program for processing data, wherein the computer readable program when executed on a computer causes the computer to perform the steps of:
organizing medical information in a concept frame data structure, which organizes the medical information for a single pathological or anatomical entity and includes medical measurements and related metadata;
analyzing the medical information to extract further information using information extractors and storing extracted medical information in the concept frame; and
storing references to appropriate visualization methods along with an associated concept in the concept frame by relating concept frames for different pathological or anatomical entities at a given time according to knowledge extracted from medical ontologies to construct a Concept-Graph of a patient at that time.

11. A method for processing data, comprising:
organizing medical information in a non-transitory computer readable storage medium in a concept frame data structure, which organizes the medical information for a single pathological or anatomical entity and includes medical measurements and related metadata;
analyzing the medical information to determine relevant analytics that can be applied to the concept frame to extract further information; and
applying the analytics to the concept frame to generate a concept graph for a given patient event by relating concept frames for different pathological or anatomical entities at a given time according to knowledge extracted from medical ontologies to construct the concept graph of a patient at that time, the concept graph representing related medical information existing in different modes, which are associated with a given concept for the concept frame.

12. The method as recited in claim 11, wherein the different modes include content of one or more of text, images, and lab data.

13. The method as recited in claim 11, further comprising:
providing temporal records of the patient in an Information Cylinder, which is a sequence of concept graphs, where each element of the sequence represents a different patient event; and
providing access to an evolution pattern of an attribute of a concept through interaction with the Information Cylinder.

14. The method as recited in claim 11, wherein the concept graph displays one or more of:
extracted medical text information;
extracted medical image information;
extracted medical text information over time, so that a user can select a time point and view the relevant text information organized in categories;
extracted medical image information over time, so that the user can select a time and view relevant image information; and
highlighted regions of images showing regions of the image where particular medical information has been detected.

15. The method as recited in claim 11, further comprising:
displaying pairs of images from different time points so that the images can be compared in real time.

16. An analytic processing system, comprising:
an analytics repository configured to store one or more analytical programs in a non-transitory computer readable storage medium to analyze medical information;
a workflow mediator implemented in software on a program storage media and configured to receive information source data structures and concept frame data structures to build an analysis request, wherein the concept frame data structures organize medical information for a single pathological or anatomical entity;
a pipeline manager implemented in software on a program storage media and configured to receive the analysis request and determine relevant analytics from the analytics repository to be used to analyze the information source data structures and the concept frame data structures; and an unstructured information management architecture (UIMA) configured to classify, organize and extract additional data from medical information in the information source data structures and the concept frame data structures and render the medical information in a graphical context, the graphical context including a Concept-Graph of a patient at a given time such that the Concept-Graph relates concept frames for different pathological or anatomical entities at the given time according to knowledge extracted from medical ontologies.

17. The system as recited in claim 16, wherein the medical information includes one or more of text, images, and lab data.

18. The system as recited in claim 16, wherein the medical information includes metadata including one or more of date, physician, and laboratory.

19. The system as recited in claim 16, wherein the graphical context includes an Information Cylinder which includes a sequence of Concept-Graphs, where each element of the sequence represents a different patient event.

20. The system as recited in claim 19, further comprising a virtual control configured for searching images from different time points to visually scroll through the Information Cylinder.

21. The system as recited in claim 16, wherein the medical information includes one or more of:

extracted medical text information; extracted medical image information; extracted medical text information over time, so that a user can select a time point and view the relevant text information organized in categories; extracted medical image information over time, so that the user can select a time and view relevant image information; and highlighted regions of images showing regions of the image where particular medical information has been detected.

22. The system as recited in claim 16, further comprising a database configured to store the concept frame data structures to organize the medical information by permitting editing and aggregating by medical personnel.

23. The system as recited in claim 16, further comprising:

a query and result mediator configured to retrieve the concept frame data structures from a database relevant to a patient visit and/or to retrieve a set of concept frame data structures over a period of time to permit display of changes in a patient's condition.

* * * * *